(12) United States Patent
Heipl et al.

(10) Patent No.: US 9,650,730 B2
(45) Date of Patent: *May 16, 2017

(54) MEDICAL IMPLANT, A KIT AND A METHOD OF MANUFACTURING A 3D FABRIC OF STRANDS FOR FORMING A MEDICAL IMPLANT

(71) Applicant: Occlutech Holding AG, Schaffhausen (CH)

(72) Inventors: Michael Heipl, Erfurt (DE); Sebastian Tilchner, Jena (DE); Kathrin Schmidt, Kahla (DE); Rüdiger Ottma, Großschwabhausen (DE)

(73) Assignee: Occlutech Holding AG, Schaffhausen (CH)

( * ) Notice: Subject to any disclaimer, the term of this patent is extended or adjusted under 35 U.S.C. 154(b) by 344 days.

This patent is subject to a terminal disclaimer.

(21) Appl. No.: 14/354,516

(22) PCT Filed: Oct. 26, 2012

(86) PCT No.: PCT/EP2012/071277
§ 371 (c)(1),
(2) Date: Apr. 25, 2014

(87) PCT Pub. No.: WO2013/060855
PCT Pub. Date: May 2, 2013

(65) Prior Publication Data
US 2014/0296909 A1    Oct. 2, 2014

Related U.S. Application Data

(60) Provisional application No. 61/551,995, filed on Oct. 27, 2011, provisional application No. 61/556,297, (Continued)

(30) Foreign Application Priority Data

Dec. 23, 2011 (EP) ..................... 11195712
Feb. 29, 2012 (EP) ..................... 12157605

(51) Int. Cl.
*D04C 3/48* (2006.01)
*A61B 17/00* (2006.01)
(Continued)

(52) U.S. Cl.
CPC ............ *D04C 3/48* (2013.01); *A61B 17/0057* (2013.01); *A61B 17/12122* (2013.01);
(Continued)

(58) Field of Classification Search
CPC ........ A61B 17/0057; D04C 3/08; D04C 3/48; D04C 1/06; D03D 3/02
See application file for complete search history.

(56) References Cited

U.S. PATENT DOCUMENTS 4,893,543 A  *  1/1990  Phillips ................ D04C 7/00
                                                        87/33
5,382,259 A     1/1995  Phelps et al.
(Continued)

FOREIGN PATENT DOCUMENTS

DE     102008015781 A1    10/2009
DE     102010019365 A1     6/2011
(Continued)

OTHER PUBLICATIONS

WIPO, European International Search Authority, International Search Report mailed Sep. 4, 2013 in International Patent Application No. PCT/EP2012/071277, 7 pages.

*Primary Examiner* — Shaun R Hurley
(74) *Attorney, Agent, or Firm* — Inskeep IP Group, Inc.

(57) ABSTRACT

The disclosure relates to a method of manufacturing a medical implant or structures for a medical implant. Dis-
(Continued)

closed is an improved occluder (1), which does not damage the surrounding body tissue. In one embodiment, a method of manufacturing a 3D fabric of strands for forming an occluder is provided. The method comprises intertwining the strands along a length of the 3D fabric for forming a primary 3D fabric structure. The intertwining is non-continuous, i.e. the braiding procedure can be halted, for forming a secondary structure of the 3D fabric without intertwining.

27 Claims, 14 Drawing Sheets

Related U.S. Application Data filed on Nov. 7, 2011, provisional application No. 61/563,332, filed on Nov. 23, 2011, provisional application No. 61/600,730, filed on Feb. 20, 2012.

(51) Int. Cl.
| | | |
|---|---|---|
| *A61B 17/12* | (2006.01) | |
| *D04C 1/06* | (2006.01) | |
| *D03D 3/02* | (2006.01) | |
| *D04C 3/08* | (2006.01) | |
| *D06B 1/00* | (2006.01) | |

(52) U.S. Cl.
CPC ......... *A61B 17/12172* (2013.01); *D03D 3/02* (2013.01); *D04C 1/06* (2013.01); *D04C 3/08* (2013.01); *D06B 1/00* (2013.01); *A61B 2017/00526* (2013.01); *A61B 2017/00575* (2013.01); *A61B 2017/00592* (2013.01); *A61B 2017/00597* (2013.01); *A61B 2017/00601* (2013.01); *A61B 2017/00606* (2013.01); *D10B 2509/08* (2013.01)

(56) References Cited

U.S. PATENT DOCUMENTS

| | | | |
|---|---|---|---|
| 6,792,979 B2 * | 9/2004 | Konya | A61F 2/90 140/92.1 |
| 2009/0157158 A1 * | 6/2009 | Ondracek | A61F 2/90 623/1.2 |
| 2009/0198315 A1 * | 8/2009 | Boudjemline | A61F 2/2418 623/1.2 |
| 2010/0191319 A1 * | 7/2010 | Lilburn | D04C 1/06 623/1.15 |
| 2011/0046662 A1 * | 2/2011 | Moszner | A61B 17/0057 606/213 |
| 2014/0296908 A1 * | 10/2014 | Ottma | A61B 17/0057 606/213 |

FOREIGN PATENT DOCUMENTS

| | | |
|---|---|---|
| WO | WO2008/040555 A2 | 4/2008 |
| WO | WO2008051279 A1 | 5/2008 |
| WO | WO2008/151204 A1 | 12/2008 |
| WO | WO2011/057002 A2 | 5/2011 |

\* cited by examiner

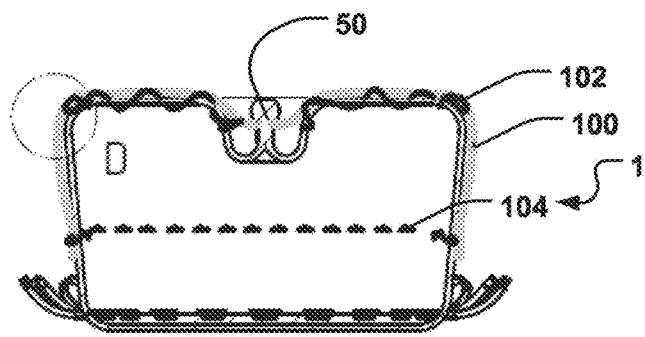
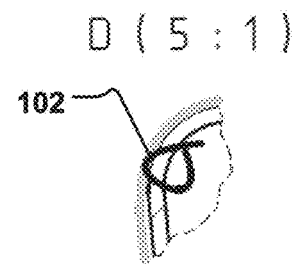
Fig. 8   Fig. 9
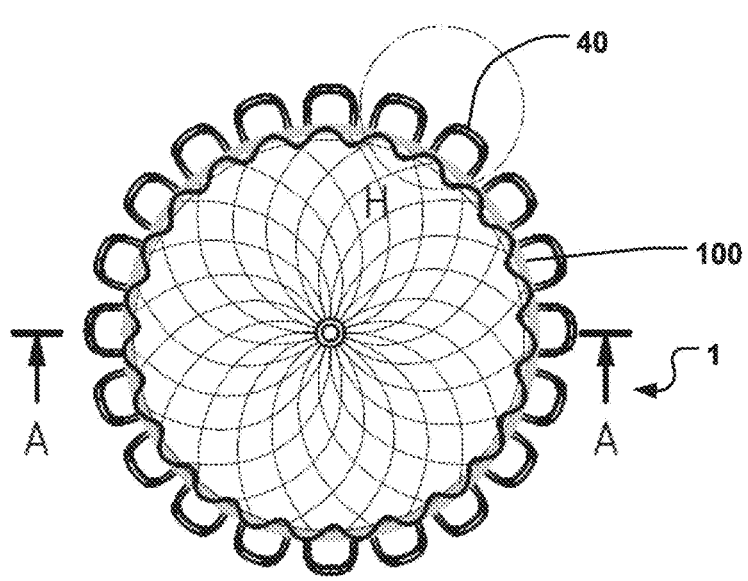
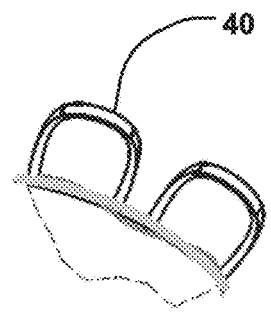
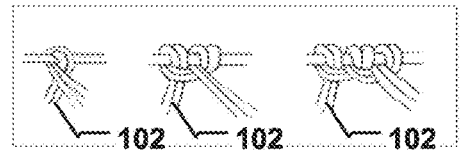
Fig. 10   Fig. 11   Fig. 12

MEDICAL IMPLANT, A KIT AND A METHOD OF MANUFACTURING A 3D FABRIC OF STRANDS FOR FORMING A MEDICAL IMPLANT

RELATED APPLICATIONS

This application is the U.S. National Phase of and claims priority to International Patent Application No. PCT/EP2012/071277, International Filing Date Oct. 26, 2012, entitled A Medical Implant, A Kit And A Method Of Manufacturing A 3D Fabric Of Strands For Forming A Medical Implant, which claims benefit of U.S. Provisional Application Ser. No. 61/551,995 filed Oct. 27, 2011 entitled Occlusion Device; U.S. Provisional Application Ser. No. 61/556,297 filed Nov. 7, 2011 entitled Occlusion Device; U.S. Provisional Application Ser. No. 61/563,332 filed Nov. 23, 2011 entitled A Medical Implant, A Kit And A Method Of Manufacturing A 3D Fabric Of Strands For Forming A Medical Implant; European Application No. EP11195712.2 filed Dec. 23, 2011 entitled A Medical Implant, A Kit And A Method Of Manufacturing A 3D Fabric Of Strands For Forming A Medical Implant; U.S. Provisional Application Ser. No. 61/600,730 filed Feb. 20, 2012 entitled A Medical Implant For Occluding An Opening In A Body And A Method Of Producing Such A Medical Implant; and European Application No. EP12157605.2 filed Feb. 29, 2012 entitled A Medical Implant For Occluding An Opening In A Body And A Method Of Producing Such A Medical Implant; all of which are incorporated herein by reference in their entireties.

BACKGROUND OF THE INVENTION

Field of the Disclosure

This disclosure pertains in general to the field of medical implants and methods therefore. More particularly, the disclosure relates to a method of manufacturing a medical implant or structures for a medical implant. Even more particularly the disclosure relates to manufacturing of structures for cardiovascular interventions, in particular embodiments provided as left atrial appendage occluders or left auricular appendix occluders.

Description of the Prior Art

An occluder is a medical product or implant used for occluding defects e.g. in the human heart. Defects may occur in various regions of the heart and have different forms. Defects in the septum of the atrium are common.

The occluders can be inserted using minimally invasive cardiac catheter techniques, more precisely by means of a transvenous, catheter-interventional access.

Being projections from the atria, auricles are parts of the heart and not defects. In the case of patients who are susceptible to atrial fibrillation or suffering from arrhythmia, the auricle may be the origin of blood clots. Thus, occluding the left auricle can prevent the creation of thrombi and reduce the risk of a stroke.

There are some left atrial appendage (LAA) occluders known for this purpose. However, it may be difficult to make the LAA occluders stay in the right position once implanted. The LAA occluder in US2011054515 A solves this by the use of barbs. Another LAA occluder is known from EP2263553 A. In this document, the positioning of the occluder is secured by the use of hooks. However, the use of hooks or barbs for securing the positioning of an occluder may damage the body tissue surrounding the barbs or hooks. This is in particular true for LAA defects which often have a very thin surrounding tissue. Aneurism penetration is another issue to be avoided in an example. Penetration of surrounding tissue by barbs may cause undesired leakage through the puncture site, e.g. into the interior of the endocardial sack surrounding the heart muscle.

JP 2004/049806 A discloses a stent for insertion into a tubular-shaped organ, such as a blood vessel of a human body. The stent has a U-shaped member, which is entwined with a peripheral section of an intersection (refer to abstract). The purpose of the U-shaped member is to hold the different sections together, not to secure the position of the stent.

Thus, there is a need for another mechanism for securing a position of the occluder. This is particularly important for LAA occluders, since the left atrial wall is rather thin and should preferably not be perforated.

Hence, an improved occluder, which upon implantation does not damage the surrounding body tissue, would be advantageous.

SUMMARY OF THE INVENTION

Accordingly, embodiments of the present disclosure preferably seek to mitigate, alleviate or eliminate one or more deficiencies, disadvantages or issues in the art, such as the above-identified, singly or in any combination by providing a method of manufacturing a kit and a medical implant, according to the appended patent claims.

According to one aspect of the disclosure, a method of manufacturing a 3D fabric of strands for forming a medical implant is provided. The method comprises intertwining the strands along a length of the 3D fabric for forming a primary 3D fabric structure. The intertwining is non-continuous. For example, the intertwining can be interrupted along the length, i.e. the braiding procedure can be halted, for forming a secondary structure of the 3D fabric without intertwining.

According to another aspect of the disclosure, a kit for manufacturing a medical implant with a non-continuous method is provided. The kit comprises a plurality of strands for braiding. It also comprises a braiding cylinder with a braiding head of an appropriate diameter, which is adaptable to a braiding machine. Furthermore, a crown-shaped holder for holding a plurality of strand loops is comprised in the kit. The kit also comprises a ring for fixation of strand loops.

Further embodiments of the disclosure are defined in the dependent claims, wherein features for the second and subsequent aspects of the disclosure are as for the first aspect mutatis mutandis.

Some embodiments of the disclosure provide for that no damage is done to body tissue by elements used for securing the position of the medical implant, since no barbs or hooks are used for this purpose.

Some embodiments of the disclosure provide for that pericardial effusion is avoided.

Some embodiments of the disclosure provide for that the medical implant is retrievable without injuring, since no barbs or hooks are used.

Some embodiments of the disclosure provide for prevention of slipping or unwanted movement of the medical implant.

Some embodiments of the disclosure provide for avoiding perforation of the thin left atrial wall, since no barbs or hooks are used.

Some embodiments of the disclosure provide for that shaping of strand loops can be made accurately, fast and/or easily.

Some embodiments of the disclosure provide for easily connecting the medical implant to e.g. a guide wire and/or for easy retrieval of the medical implant.

Some embodiments of the disclosure provide for a sinking of the coupling towards the centre of the medical implant, when the medical implant is compressed.

Some embodiments of the disclosure provide for fast, accurate and/or easy manufacturing.

The use of a coating outside an external surface of a medical implant provides for a lower friction of the medical implant in e.g. a catheter.

Some embodiments of the disclosure also provide for an improved occlusion.

Some embodiments of the disclosure also provide for improved sealing of a defect, such as a heart defect.

Some embodiments of the disclosure also provide for an improved endothelialization.

Some embodiments of the disclosure also provide for slowing down the blood flow through the defect.

Some embodiments of the disclosure also provide for an advantageous and/or easier delivery of the medical implant, since the use of a coating outside an external surface of a medical implant may make the medical implant glide or slide easier through a delivery catheter.

Some embodiments of the disclosure also provide for enabling an initial controllable fluid retention.

Some embodiments of the disclosure also provide for that an inflow of blood to different areas of a medical implant is controlled or controllable.

Some embodiments of the disclosure also provide for that the flow is efficiently restricted by covering at least substantially the full diameter of both ends of the medical implant.

Some embodiments of the disclosure also provide for that integration of the medical implant with surrounding blood is enhanced.

Some embodiments of the disclosure also provide for that the coating or the non-fibrous membrane is free of tension, so that pre-mature fatigue thereof can be avoided and thus a reliable ingrowth is allowed for.

Some embodiments of the disclosure also contribute to facilitation of expansion into an expanded shape, since the coating elastically contributes to expansion into the expanded shape, i.e. by making the coating elastic and by applying the coating to the medical implant, while the medical implant is in its expanded shape, the coating on the external surface of the medical implant is prone to contribute to force the medical implant into its expanded shape.

Some embodiments of the disclosure also provide for facilitation of the delivery of the medical implant through a catheter, since the coating is prone to contribute to force the medical implant into its contracted shape if the coating is applied to the medical implant while the medical implant is in its contracted shape.

Some embodiments of the disclosure also provide for that the occlusion is not abrupt upon implantation.

Some embodiments of the disclosure also provide for that a certain blood flow may still occur after implantation and gradually decline upon blood coagulation and/or endothelialization of the implanted medical implant.

Some embodiments of the disclosure also provide for that friction of the medical device is lowered, e.g. during delivery through a catheter.

Some embodiments of the disclosure also provide for that cellular biocompatibility is maximized.

Some embodiments of the disclosure also provide for a medical implant, which is easier and cheaper to manufacture than a medical implant having patches inside, since no sewing is necessary.

Some embodiments of the disclosure also provide for a less time consuming manufacturing of a medical implant.

Some embodiments of the disclosure also provide for a very flexible medical implant.

Some embodiments of the disclosure also provide for a medical implant with a particularly large expansion/contraction ratio.

It should be emphasized that the term "comprise/comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the disclosure are capable of will be apparent and elucidated from the following description of embodiments of the present disclosure, reference being made to the accompanying drawings, in which

FIG. 8 is a lateral view of a medical implant with a membrane;

FIG. 9 is a view of a thread used for attaching a membrane to a medical implant;

FIG. 10 is a top view of a medical implant with strand loops;

FIG. 11 is a detailed view of strand loops of a medical implant;

FIG. 12 is a view of different knots used for attaching a membrane to a medical implant;

DESCRIPTION OF THE PREFERRED EMBODIMENTS

Figure 5:
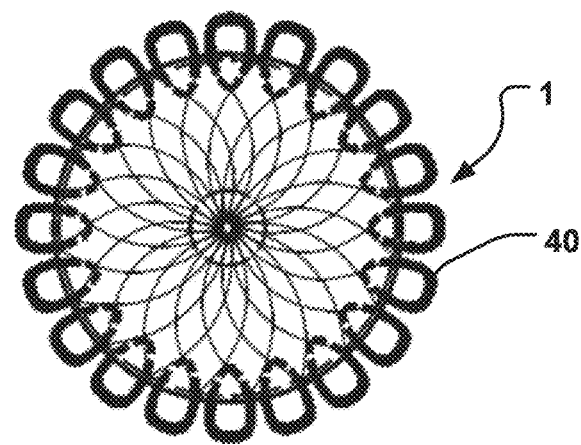
FIG. 5 is a top view of another medical implant.

Specific embodiments of the disclosure will now be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the disclosure. In the drawings, like numbers refer to like elements.

The following description focuses on an embodiment of the present disclosure applicable to medical implants and in particular to a left atrial appendage (LAA) occluder. However, it will be appreciated that the disclosure is not limited to this application but may be applied to many other medical implants including for example Filters, Stents, Vascular Occluders, Products for treatment of aneurysm, Plugs and Occlusion systems for other applications, such as atrial septal defect (ASD) occluders, Patent foramen ovale (PFO) occluders, paravalvular leakage (PLD) occluders and ventricular septal defect (VSD) occluders.

Figure 1:
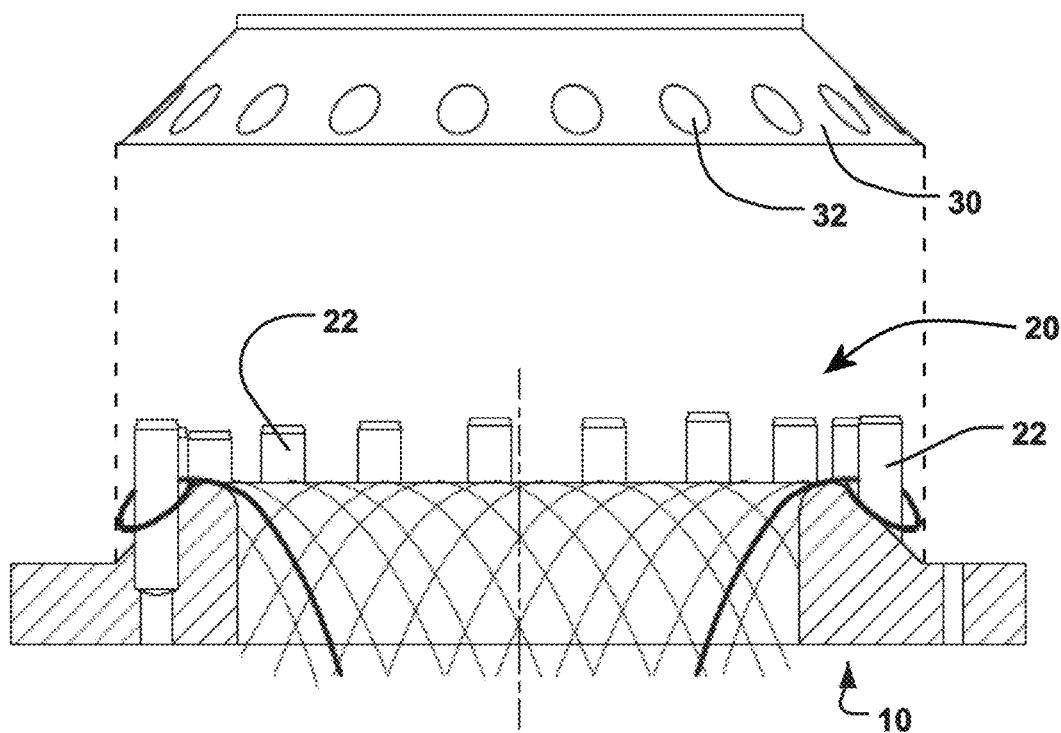
FIG. 1 is a lateral view of a braiding head with a crown-shaped holder and a ring.

In FIG. 1, a braiding head 10 of a braiding machine for braiding a medical implant is shown. The braiding head 10 is equipped with a crown-shaped holder 20. The crown-shaped holder comprises a number of pins 22 distributed evenly around the crown-shaped holder 20. On top of the braiding head 10, a ring 30 can be placed. The ring 30 has holes 32 corresponding to the pins 22 of the crown-shaped holder 20.

Figure 2:
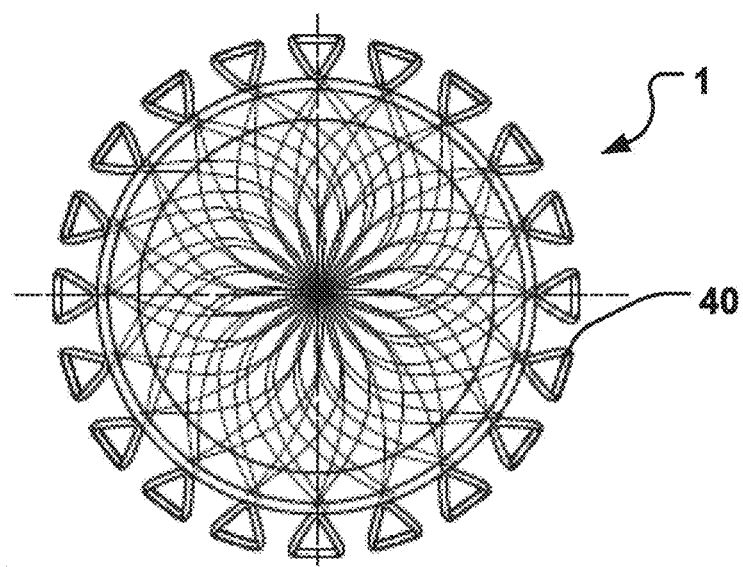
FIG. 2 is a top view of a medical implant.

One embodiment is depicted in FIG. 2. FIG. 2 is a top view of a medical implant 1, such as an LAA occluder. This figure shows a medical implant 1 comprising strand loops 40. The strand loops 40 prevent the medical implant 1 from slipping and/or moving from the position once implanted, since the strand loops can fixate the medical implant to a body wall. The strand loops 40 are loops made from strands. The strands may be made of shape-memory materials, metal, super elastic alloys, Nitinol, or polymers, such as biodegradable polymers. Thus, the strands may be wires. If the strands are made of Nitinol, then the strands may be heat-treated and a very flexible self-expanding wire-mesh can be obtained.

Figure 3:
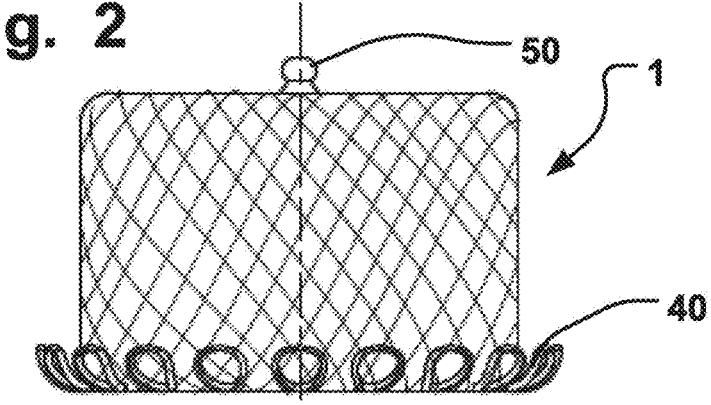
FIG. 3 is a lateral view of a medical implant.

FIG. 3 is a lateral view of a medical implant 1. In this embodiment the loops 40 are located at one side of the medical implant and the coupling 50 on the opposite side of the medical implant 1. However in another embodiment, the strand loops 40 may be positioned on the same side of the medical implant as the coupling 50.

Figure 4:
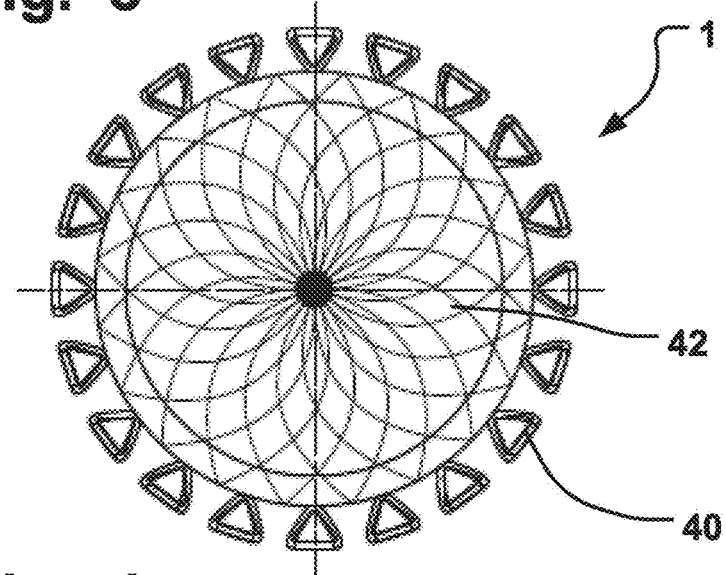
FIG. 4 is a view of a medical implant from below.

FIG. 4 is a view of a medical implant from below and depicts another embodiment of this disclosure. In this embodiment the strand loops 40 are of a shape that extends out of a plane perpendicular to the longitudinal axis of the medical implant 1. More precisely, the peripheral edges are bent out of the perpendicular direction towards an end of the device. The shape looks in the illustration like triangular strand loops that may be rounded at the corners. They may be in examples. However, the illustration of embodiments given is round or oval shaped in a desired 3D shape. By shaping the strand loops 40 in this manner, the stabilization of the medical implant 1 will be further improved, and thus the medical implant 1 is further prevented from slipping and/or moving from the position once implanted. By the use of thus shaped strand loops, the retention may be improved. The bent peripheral edges of the strand loops 40 provide for a defined outwardly oriented spring like force when implanted. The spring force is preferably much lower than the force of the medical device for returning to an expanded shape from a collapsed shape. In addition, the loops provide for a controllable spring force irrespective of the main body of the implant 1 being fully expanded.

The spring force of the loops may be provided in a radial direction and an axial direction thanks to the advantageous bending of the peripheral edge. As the number and shape of the loops may be varied, a large flexibility and adaptability to different defects to be occluded is provided in a cautious and reliable manner by embodiments of the device 1.

FIG. 5 is a top view of another medical implant. In this embodiment the strand loops 40 are of a round shape. By giving the strand loops 40 a round shape, the strand loops 40 are less prone to break.

Figure 6:
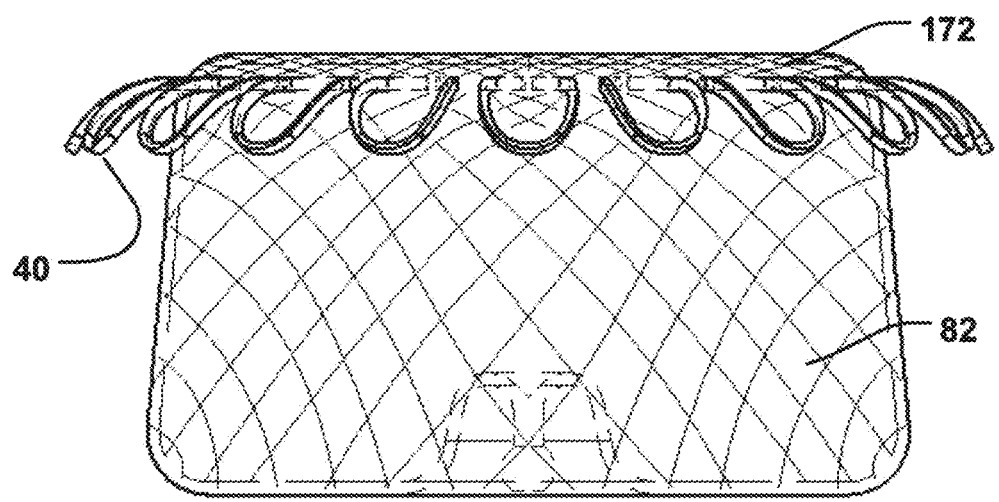
FIG. 6 is a lateral view of a medical implant.

FIG. 6 is a lateral view of a medical implant, in this case an LAA occluder, showing another embodiment. A longitudinal section 82 of the medical implant in this figure is of the form of a frustum of a hollow cone-shaped cylinder. The strand loops 40 surround the rim of the hollow cone-shaped cylinder and are extendable outwardly from the hollow cone-shaped cylinder substantially perpendicularly to a centre axis of the hollow cone-shaped cylinder. The cone shape provides for a reliable positioning avoiding embolization of the device in a defect, such as the LAA. The principle may be compared to a cork that has a larger diameter at one end.

The larger diameter of the LAA occlude shown in FIG. 6 is upon implantation positioned at or towards the opening of the LAA.

The medical implant may also be of another shape. It can consist of different sections, whereof some sections are cone-shaped and other sections are disc-shaped.

Figure 7:
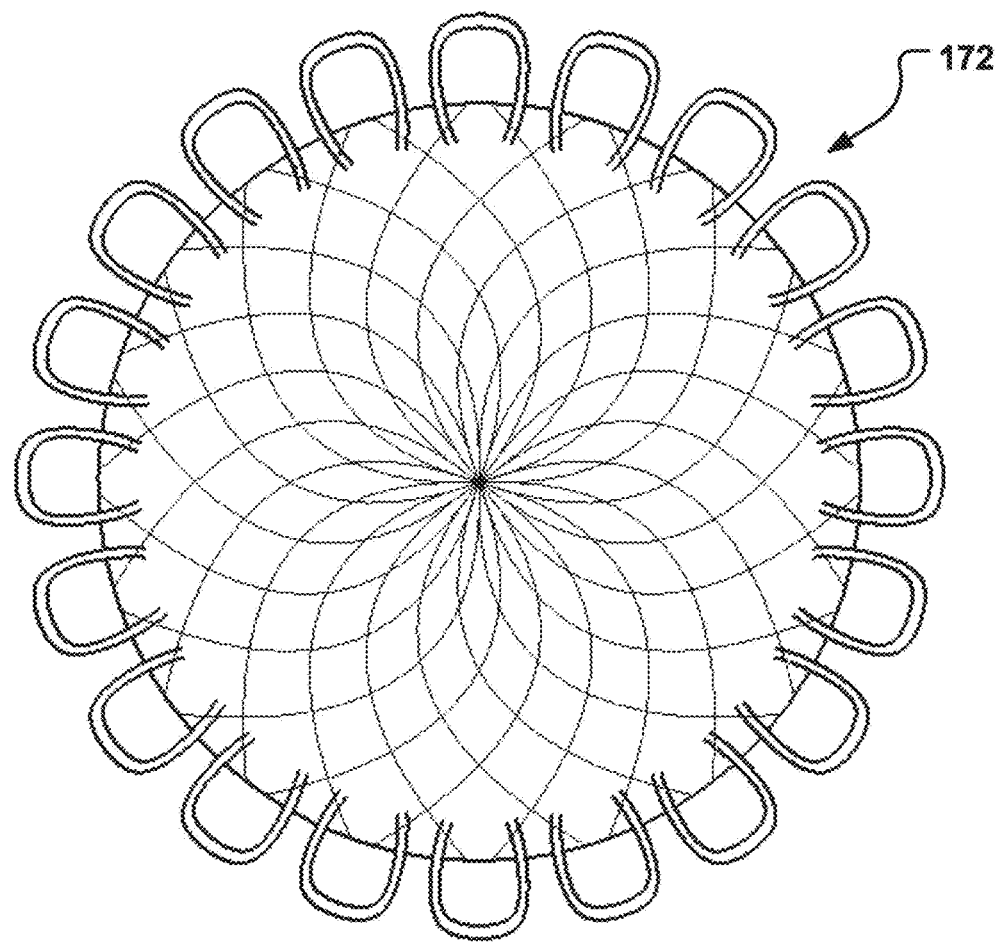
FIG. 7 is a top view of a medical implant.

FIG. 7 is a top view of a medical implant. In one embodiment, shown in FIG. 7, half the strands, which will also be used for the longitudinal section 82, form a cover for the medical implant on the proximal side 172. The remaining strands, which will also be used for the longitudinal section 82, project outwards on the edge of the cover as strand loops 40. Thus, on the proximal side 172, strands which form the strand loops 40 are not integrated in the braid. On a distal side, opposite to the proximal side 172, as well as along the longitudinal section 82, all strands from the outer edge up to the rotation axis are braided or intertwined. Thus, the configuration or distribution of strands to strand loops can be said to be 2:1. However, it is also possible to have other distributions, such as 1:1, 1:2, 1:3, 3:1 etc. It is also possible to make a medical implant, which has only strand loops on the proximal side 172, i.e. forming an open mesh or a round longitudinal braid, closed on one side only.

FIG. 8 is a lateral view of a medical implant with a membrane 100. The membrane 100 may be attached to the medical implant 1 with a strand or thread 102. In this embodiment, the membrane is attached to the outer surface of the medical implant, on the same side as the coupling 50. The membrane 100 can cover the whole circumference of the medical implant 1 and is then also stitched to the medical implant 1 with a seam 104. The use of membranes or inner membranes results in improved occlusion and rapid endothelialisation. The use of a membrane also results in an ideal closure of e.g. the left atrial appendage, since it seals the gap instantly.

FIG. 9 is a view of a thread used for attaching a membrane to a medical implant. The thread 102 is wound around at least one strand of the medical implant.

FIG. 10 is a top view of a medical implant 1 with strand loops 40. The strand loops 40 are located all around the medical implant 1. Also the membrane 100 can be seen in FIG. 10. Here the membrane 100 covers the whole circumference of the medical implant 1.

FIG. 11 shows the strand loops 40 of the medical implant 1 more in detail. The strand loops 40 in FIG. 11 have a rounded shape, i.e. a somewhat rectangular shape with rounded corners. Rounded corners are tissue friendly avoiding deep tissue penetration and possible ruptures or leakages.

FIG. 12 is a view of different knots used for attaching a membrane to a medical implant. The thread 102 can be secured to a strand of the medical implant 1 with a single knot or with a double knot. The ends of the thread 102 can be thermally treated to provide further reliability of the fixation.

Figure 13:
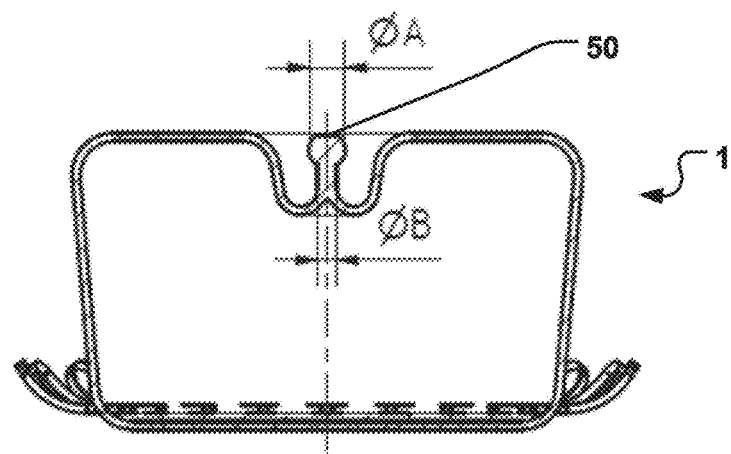
FIG. 13 is lateral view of a medical implant with a coupling.

FIG. 13 is lateral view of a medical implant with a coupling 50. The coupling 50 is in the shape of a ball pivot. The ball pivot can be connected to a flexible pusher, which can be used to move the medical implant in a sheath e.g. for delivery of the medical implant and/or retrieval of the medical implant prior to being decoupled. The coupling 50 is in this embodiment sunk or lowered into the medical implant 1 and will not impede blood flow at the target site, e.g. in a body vessel, where it is situated after having been delivered. In this embodiment, the medical implant has been braided so as to form a hollow space for the coupling 50. The advantage offered by the lowered coupling 50 is that the medical implant is not lengthened when the shaft is compressed, i.e. when the medical implant is radially compressed. Thus, the coupling is not moving out of its position, and will therefore not impede blood flow. In another embodiment according to FIG. 14, a proximal side 172 is instead given a concave shape to assure a sinking of the coupling 50, when the medical implant is radially compressed. With the coupling 50, the flexibility during delivery is increased, since the medical implant 1 is retrievable.

Figure 14:
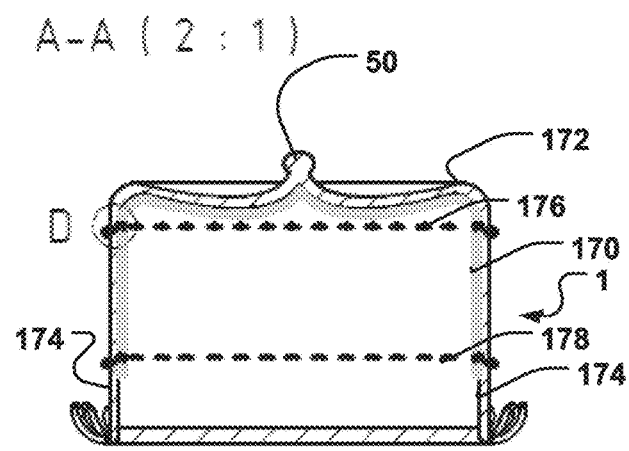
FIG. 14 is a lateral view of a medical implant with a membrane.
Figure 25A:
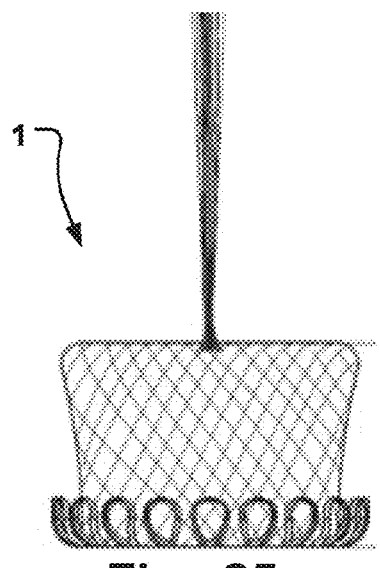
FIG. 25a shows the concave shape of an medical implant.
Figure 25B:
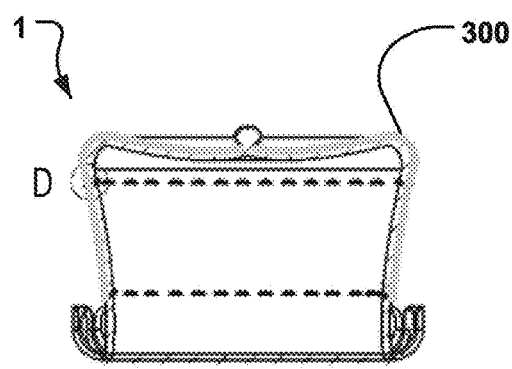
FIG. 25b shows a medical implant with an outer membrane.

In an embodiment depicted in FIG. 14, the medical implant has a membrane 171. The membrane is an inner membrane 170. The inner membrane may be a special thermo-treated PET-knit fabric. The inner membrane 170 is attached to the inner surface of the medical implant 1. The inner membrane 170 may be attached to the medical implant 1 with a strand or thread. In this embodiment, the inner membrane 170 is attached to the inner surface of the medical implant 1, on the same side of the medical implant 1, as the coupling 50, i.e. the proximal side 172 of the medical implant 1, and extending in a longitudinal direction along the longitudinal sides 174 of the medical implant 1. The inner membrane 170 can cover the whole circumference of the medical implant 1 and is then also stitched to the medical implant with seams 176, 178. The use of membranes and/or inner membranes results in improved occlusion and rapid endothelialisation. In another embodiment depicted in FIG. 25b, an outer membrane 300 is attached outside the medical implant in a similar manner as the inner membrane 170. Also the outer membrane 300 may be a special thermo-treated PET-knit fabric. In one embodiment, the medical implant is covered with membranes both on the inside and the outside of the braiding. As an alternative of using membranes, the medical implant may instead be covered or coated using Nano-spinning or a dipping method. The coating as well as the membranes may be made of a biocompatible and implantable material, such as PTE, PTFE or PUR. The inner and/or outer membrane or coating may be provided as a non-fibrous film membrane that may have an initial controllable fluid retention by perforations or microperforations thereof. The membrane may cover the entire expanded diameter of the implant. Alternatively, it may only cover portions thereof. The portions may be as small as the cell structure of the fabric of the implant 1. For instance one or more cells of a braiding may be provided with a coating extending the space between adjacent strand portions forming the cells.

In this manner, different perfusion rates may be adjusted to different areas of the device. It may for instance be desired to obtain an inflow of blood into the inner of the expanded device from a distal end thereof to enhance integration of the device with surrounding blood upon clotting thereof. A reduced or prohibited outflow of blood through the proximal end may however be provided by a tighter membrane or larger diameter/surface/cells of the device being covered than those of another section of the implant 1.

The coating or external membrane may be affixed to the implant 1 in its expanded shape. In this manner, the coating or membrane is free of tension which advantageously avoids pre-mature fatigue thereof allowing for a reliable ingrowth.

The coating or external membrane may alternatively be affixed to the implant 1 in its collapsed shape.

Patterns of covered cells may be provided to efficiently control a desired flow pattern upon implantation. In this manner, the occlusion is not abrupt upon implantation. A certain blood flow may still occur after implantation and gradually decline upon blood coagulation and/or endothelization of the implanted device.

It should be noted that the aforementioned principles of coatings/membranes may be provided with other implants than the examples shown herein, e.g. ASD, PFO, PLD or VSD occluders.

Figure 15:
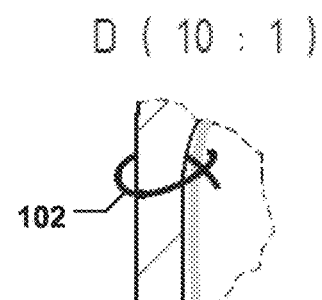
FIG. 15 is a view of a thread used for attaching a membrane to a medical implant.

FIG. 15 is a view of a thread used for attaching a membrane to a medical implant. The thread 102 is wound around at least one strand of the medical implant for attaching the membrane to the medical implant.

Figure 16:
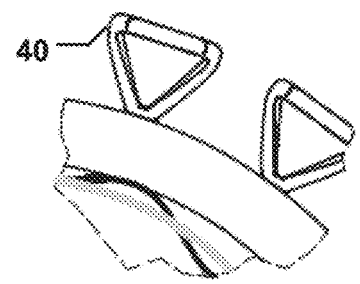
FIG. 16 is a detailed view of triangular strand loops of a medical implant.

FIG. 16 is a detailed view of strand loops 40 of a medical implant. The view in FIG. 16 corresponds to the area in FIG. 17 marked with F.

Figure 17:
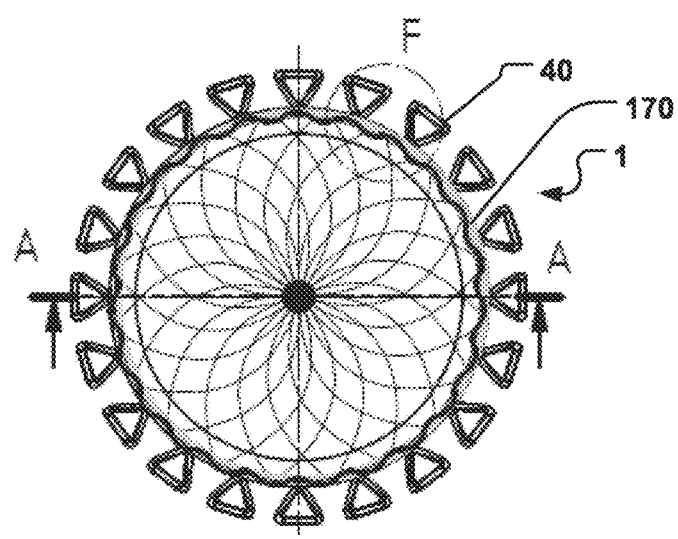
FIG. 17 is a top view of a medical implant.

FIG. 17 is a top view of a medical implant 1. The triangular strand loops 40 are located all along the perimeter of the medical implant 1. Also in FIG. 17, the inner membrane 170 can be seen.

Figure 18:
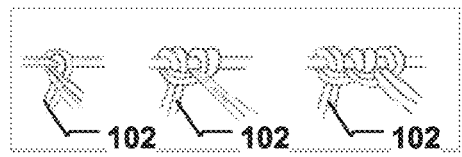
FIG. 18 is a view of different knots for a medical implant.

FIG. 18 is a view of different knots for a medical implant. The thread 102 can be secured to a strand of the medical implant 1 with a single knot or with a double knot. The ends of the thread 102 can be thermally treated.

Figure 19:
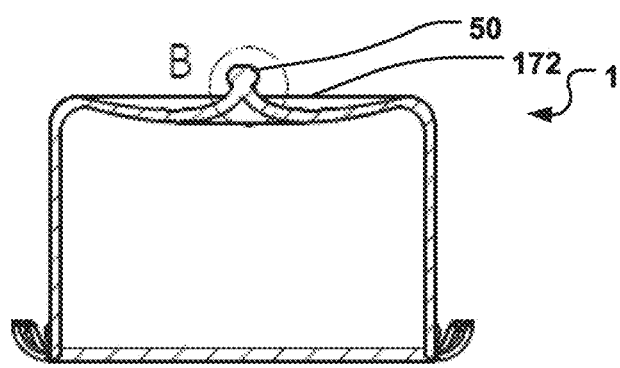
FIG. 19 is a lateral view of a medical implant with a coupling.

FIG. 19 is a lateral view of a medical implant with a coupling 50. As can be seen from this figure, the braiding of the medical implant 1 is at the proximal side 172 of the medical implant 1 formed so that the proximal side 172 can be sunk in towards a centre of the medical implant 1.

Thus, the coupling 50 extends less from the medical implant 1 and will impede the blood flow in the atrium to a lower extent, at the target site where it is situated after having been delivered, since the proximal side 172 forms the ending towards the atrium.

Figure 20:
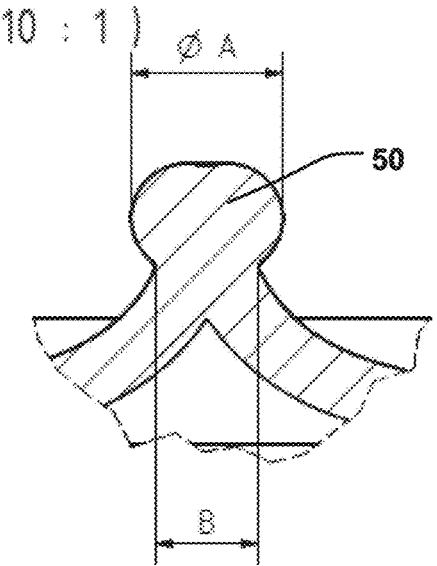
FIG. 20 is a detailed view of a coupling of a medical implant.

FIG. 20 is a detailed view of a coupling of a medical implant 1. The coupling 50 is formed by welding the strand ends together after the braiding machine has finished the braiding or intertwining of the medical implant. The coupling 50 is formed by welding it into a ball pivot. The strands are merging into the welded clot in a not-straight, i.e. not parallel manner in the example shown in FIG. 20. The ball pivot can be connected to a socket of a flexible pusher, which can be used to move the medical implant in a sheath for delivery. The pusher may be able to rotate the medical implant 360 degrees, when the ball pivot is connected to the socket. The braiding or intertwining of the medical implant 1 can be formed so that the medical implant can be inserted into the sheath. After leaving the sheath, the medical implant 1 independently reassume the predetermined shape and ensure an interlocking hold.

Figure 21:
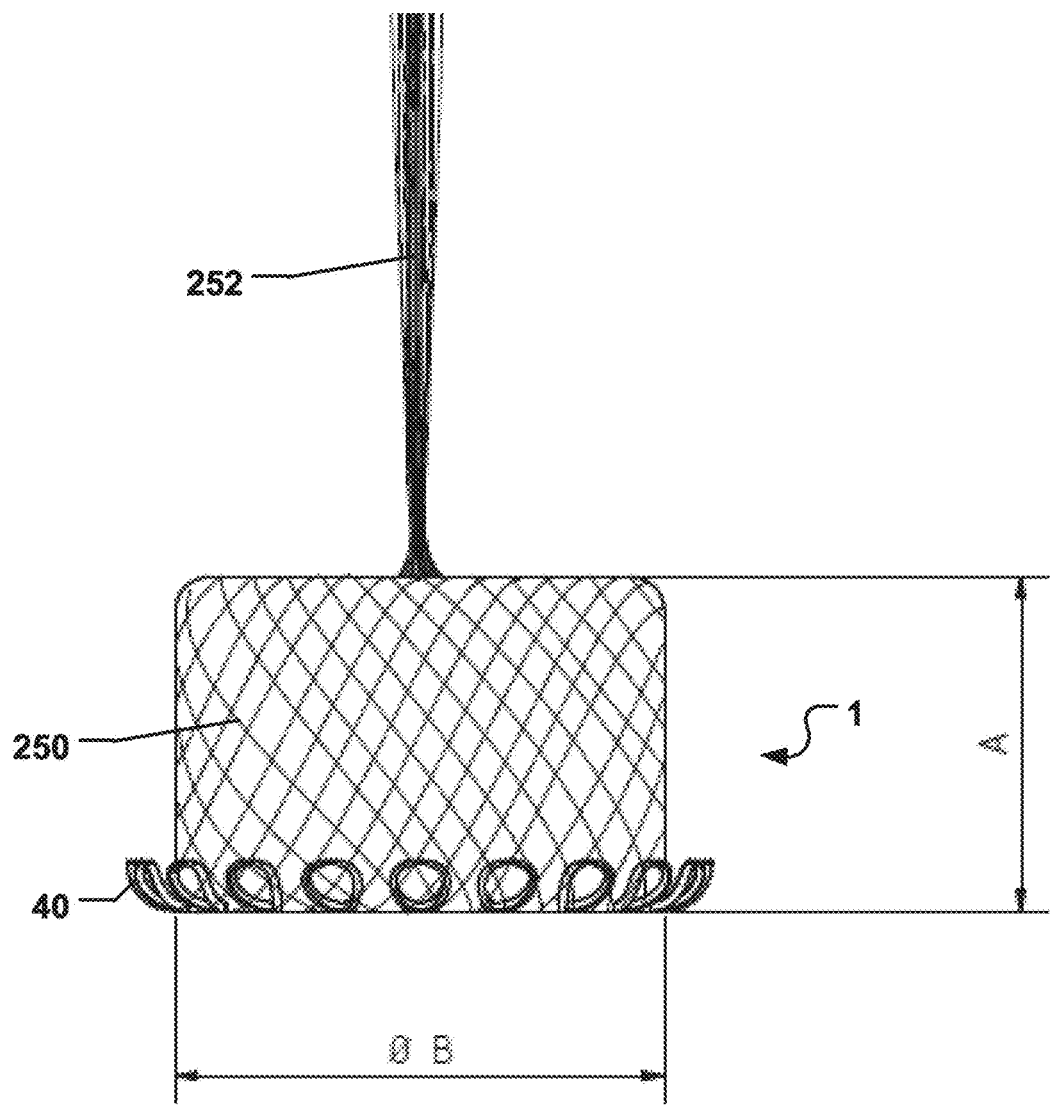
FIG. 21 is a lateral view of a medical implant being manufactured.

FIG. 21 is a lateral view of a medical implant 1 being manufactured. This figure shows the medical implant 1, after being completed. In the figure, the strands 252 are shown. The strands 252 are only for illustrative purposes shown flaring out at the end of the bundle. In practice, the bundle of strands has parallel strands. These strands 252 are cut to an appropriate length and welded together to form the coupling 50 shown in e.g. FIG. 19.

Figure 22:
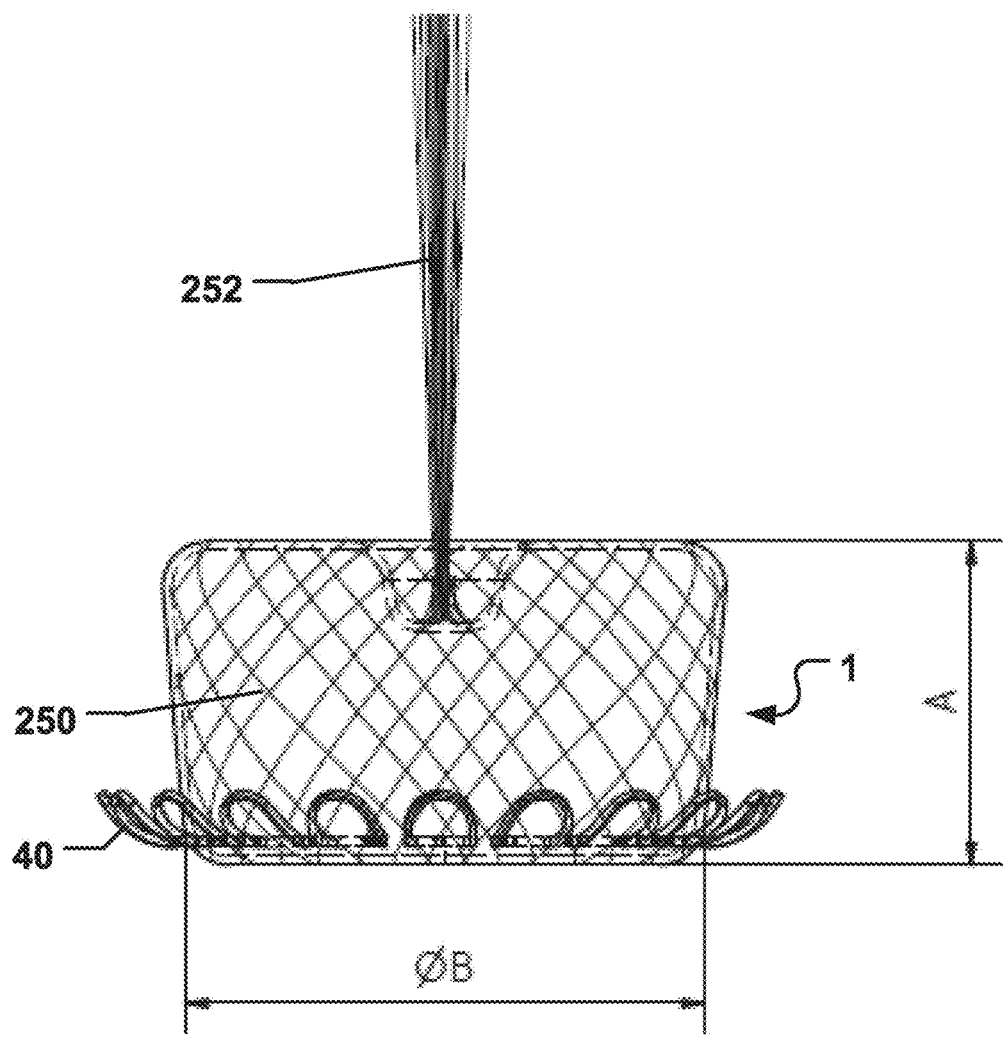
FIG. 22 is a lateral view of another medical implant being manufactured.

FIG. 22 is a lateral view of a medical implant being manufactured. This figure shows the medical implant 1, after being completed. In the figure, the strands 252 are shown. The braiding of the medical implant has here been sunk down into the medical implant so as to accommodate a hollow space for the coupling 50. The strands 252 are cut to an appropriate length and welded together to form the coupling 50 shown in e.g. FIG. 13.

Figure 23A:
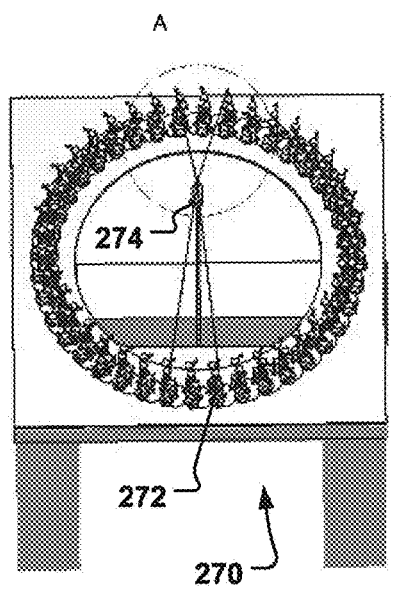
FIG. 23a is a view from above at an angle of a braiding machine.

FIG. 23a is a view from above at an angle of a braiding machine 270. The braiding machine is a round braiding machine and has a plurality of bobbins 272 arranged in a circle with a braiding head 274 of a braiding cylinder arranged inside the circle of the bobbins 272. The number of bobbins may vary according to the type of braiding machine used.

Figure 23B:
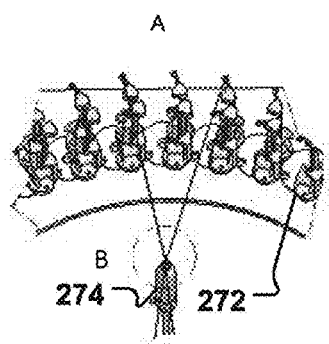
FIG. 23b is a detailed view of bobbins and a braiding head of a braiding machine.

FIG. 23b is a detailed view of the bobbins 272 and a braiding head 274 of a braiding machine. The bobbins 272 are used for keeping the strands.

Figure 24:
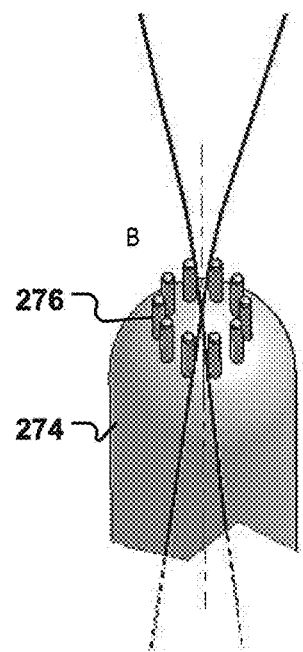
FIG. 24 is a detailed view of a braiding head.

FIG. 24 is a detailed view of a braiding head 274. One embodiment of the disclosure is a method of manufacturing a 3D fabric of strands for forming a medical implant. Examples of such medical implants are septal, ventricular or auricle appendage occluders. The method comprises intertwining the strands along a length of the 3D fabric for forming a primary 3D fabric structure. An example of such a primary structure is the structure 42 shown in FIG. 4. The intertwining is non-continuous. First, a portion, such as the proximal side 172 (shown in FIG. 6), of the primary structure is formed by intertwining strands. Then the intertwining is interrupted along the length, i.e. the braiding procedure is halted. This interruption may occur after the bobbins 272 have been rotated a quarter of a turn. Thereafter a secondary structure of the 3D fabric is formed without intertwining. The forming of the secondary structure is performed by making strand loops 40. The making of the strand loops 40 is facilitated by the use of a crown-shaped holder 20 (shown in FIG. 1). The crown-shaped holder 20 has a plurality of pins 22 distributed around it. The strands are circled around the pins 22 so as to encircle the pins 22 and form strand loops 40. The pins 22 may have a circular shape, an oval shape, a triangular shape or any other suitable shape. Although pins 22 of the same crown-shaped holder 20 normally have the same shape, it is possible to have a crown-shaped holder with pins 22 having different shapes. Thereafter, the intertwining is continued. A ring 30 of a similar size as the crown-shaped holder 20 is placed over the crown-shaped holder 20 for fixation of the strand loops, since the ring 30 is provided with holes 32 in positions along the ring 30 corresponding to positions of the pins 22 of the crown-shaped holder 20. Instead of intertwining, the primary structure may be formed by interlacing, interweaving, or braiding. The strand loops 40 prevent slipping or unwanted movement of the medical implant. Since the strand loops 40 are used instead of hooks or barbs for fixation of the medical implant after implantation, there will be no damage to body tissue as there may be if hooks or barbs are used. Thus, the risk of perforation of the thin left atrial wall is considerably lowered. Furthermore, pericardial effusion is avoided. Moreover, the medical implant may be retrievable without injuring body tissue or heart structure, since no barbs or hooks are used. Although no barbs or hooks are used, the medical implant 1 is easily fixated to a body wall and a very little gap or no gap is left in the target cavity while being sufficiently retained to allow for reliable ingrowth in a minimum of time.

In one embodiment, the bobbins of the braiding machine are driven in a certain position. The advance of the strands are set to an appropriate length of lay, e.g. the gradient of the strand windings is set, and the appropriate length of braid or intertwining is set. A braiding cylinder appropriate for the braid size is chosen from braiding cylinders with different diameters. The braiding cylinder with a braiding head 274 actuated by a feed gear mechanism is arranged in the centre of the machine. Then the strands are wound onto the bobbin coils; and the strands are routed over the thread disengagement system of the bobbins and pretensioned. A coupling used to hold the strand sections to be braided is attached to the end of the thread.

The strand sections required for the braid length are provided. The method of manufacturing comprises connecting a first end of a strand to a bobbin 272 of a round braiding machine with a plurality of bobbins 272 and a second end of said strand to a diametrically opposing bobbin 272 of said round braiding machine for a plurality of strands and arranging the middle sections of said plurality of strands in a fixed sequence over a braiding head 274 in a crisscrossed manner, i.e. there is a crisscrossed placement in a fixed sequence for half of the strands. The braiding head 274 of the braiding cylinder is equipped with pins for putting on strands in an ordered fashion. The pins are subdivided depending on the number of bobbins and the diameter of the braiding cylinder. The braiding head 274 of the cylinder may be semicircular or have planar surfaces that are rounded on the edges.

Thereafter a braiding procedure is started. After a portion of the medical implant has been braided or intertwined, the braiding procedure is halted. A crown-shaped holder 20 for holding a plurality of strand loops 40 is placed at the braiding head 274. The crown-shaped holder 20 is held centrally by a screw so that there is only a small space between the crown-shaped holder 20 and the braiding head 274, i.e. the crown-shaped holder 20 is placed at a certain axial distance from the braiding head 274.

Thereafter the remaining strand sections are individually bent in the middle sections in order to form strand loops 40. The remaining strand sections are introduced into a space between the braiding head 274 and the crown-shaped holder 20 from below. Thereafter, the strand loops 40 are guided separately through the space between the crown-shaped holder 20 and the braiding head 274. The strand loops 40 are placed over pins 22 of the crown-shaped holder 20. The strand ends are routed to the bobbins 272. Thereafter the strand ends are attached to the bobbins 272, i.e. the strand ends are connected to the clamp system of every second bobbin. Thus, the strand ends being crossed on the braiding head 274 and the strand loops 40 attached to the crown-shaped holder 20 are connected in regular correspondence with the bobbins 272. A ring 30 is placed on top of the crown-shaped holder 20 for fixation of the strand loops 40. When the ring 30 has been placed on top of the strand loops 40, the strand loops 40 are pressed down so as to be held. Then the braiding procedure is continued until an intended strand length has been braided. The strand ends are detached from the bobbins 272. Thereafter, the strand ends are attached to the ring 30 with fixation means, such as an adhesive strip. The braided material may be thermally treated together with the ring 30 and the crown-shaped holder 20 for shaping of the medical implant. The thermal treatment serves for shaping, with the braids being introduced into a device that is operative in prescribing the shape of the medical implant. Certain tools are used for this shaping and the medical implant is shaped into a conical or truncated shape in a longitudinal direction. A medical implant 1 with a conical shape can be seen in FIG. 25a. Due to the conical shape of the medical implant, higher radial forces from the body walls are possible. Therefore, the risk of perforation is lowered.

Other possible shapes of the occluder are elongated, round, cylindrical, flat or dumbbell-shaped.

Finally the strand ends, preferably all the strand ends, are welded together, by at least partly melting a length of the plurality of strands to form a defined ball pivot as a coupling 50. The method of manufacturing provides accurate, fast and easy shaping of strand loops 40.

The medial device manufactured by the above-mentioned method is rotationally symmetrical, and may be of a closed mesh-structure. When the medical implant is implanted, it is slight radial compressed. However, no proximal change in length occurs.

The medical implants are available in different sizes over a large range, with the length corresponding to substantially 1/3 of the nominal diameter. The length may vary between e.g. 10-22 mm, and the diameter between e.g. 15-39 mm. It is even possible to combine different wire gauges in one braid. The medical implants can be held in the auricle as a result of radial forces. They are distinguished by simple handling, and self-centering in the shunt. Since the braiding of the medical implant is highly flexible, the medical implant adapts well to the complex shape of the left atrial appendage.

Although the strand loops 40 are shaped so as not to damage body tissue, should barbs be needed for positioning of the medical implant, then the loops can be severed to form sharp barbs. Thus a perforation of the tissue is possible.

Although, the strand loops 40 are depicted in the figures as situated in one row, it is possible to have strand loops 40 in multiple rows, e.g. two rows.

The strand loops 40 may be situated either on the proximal side 172 or the opposite side, i.e. the distal side. It is further possible to have strand loops 40 on both the proximal side 172 and the distal side. This results in a fixation of the implanted medical device in both directions.

Figure 26A:
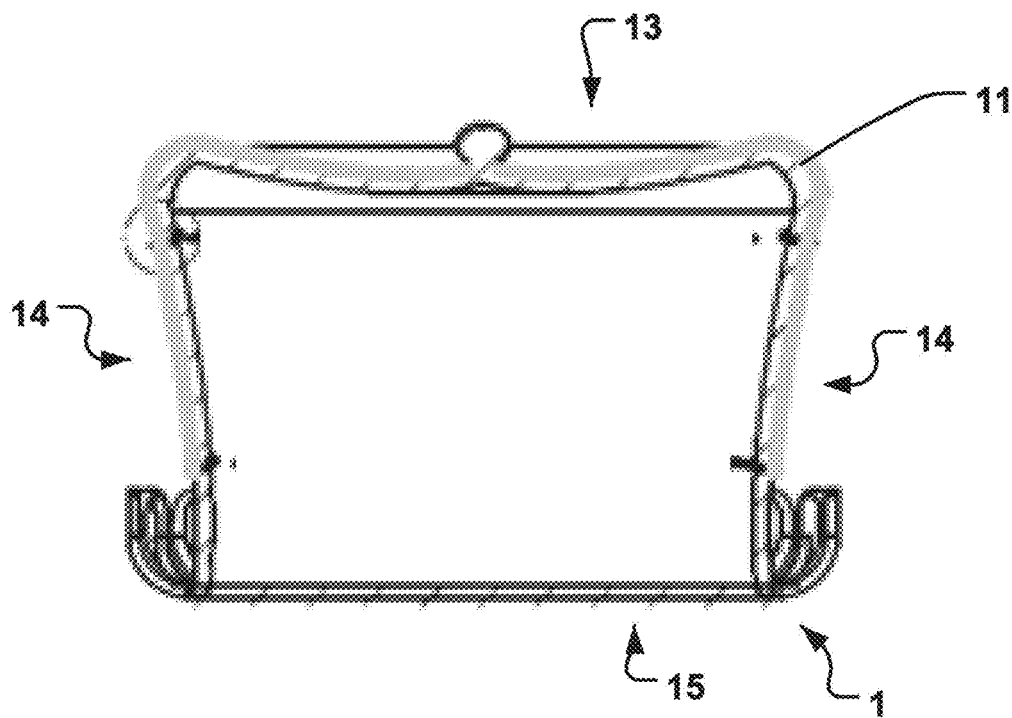
FIG. 26a is a lateral view of a medical implant with a coating outside the medical implant.

In an embodiment of the disclosure according to FIG. 26a, a medical implant 1 is provided with a coating 11. The coating 11 has been applied to an external surface of the medical implant 1. The medical implant has been coated on the outside by a method, in which the medical implant 1 has been dipped in a solution with a specific viscosity, while the medical implant 1 was in an expanded shape. By applying the coating 11 to the medical device 1, while the medical device 1 is in an expanded shape, the coating 11 is free of tension, which advantageously avoids pre-mature fatigue thereof and thus allows a reliable ingrowth. Application of a coating 11 to a medical implant 1, while the medical device 1 is in an expanded shape, may also be advantageous for other reasons, such as the fact that the medical implant 1 can be made very flexible and that a particularly large expansion/contraction ratio, i.e. a ratio of a size or diameter of the medical implant 1 in its expanded shape and the size or diameter of the medical implant 1 in its contracted shape, can be obtained for the medical implant 1.

By making sure that the solution has a specific viscosity, the coating can be made non-fibrous. The specific viscosity is a viscosity, which takes on a value, which is in an interval, where the solution for the coating is non-fibrous or not fibrous. Thus, the coating will be made fibrous. This may be advantageous, since e.g. a lower friction towards a catheter is achieved. By having a lower friction towards the walls of a delivery catheter, the delivery is facilitated and made smoother, i.e. the medical implant slides or glides more smoothly through the delivery catheter. In one embodiment only one end 13, and not the side 14 of the medical implant 1, which side 14 encircles the medical implant 1, is dipped into the solution. In another embodiment, the end 13 and part of or the whole side 14 are dipped into the solution, so as to be provided with coating. Thereby, a large portion of the medical implant 1 is covered with the coating 11. In yet another embodiment, only the ends of the medical implant 1 are dipped into the solution, i.e. the end 13 and the other end 15 are dipped into the solution, but the side 14 is not dipped into the solution. Thereby, the medical implant is covered at both ends. This can be done by first dipping the end 13 into the solution, then retracting the medical implant 1 from the solution. Thereafter, the medical implant is turned around and with the other end 15 facing the solution, the medical device is again dipped into the solution. A coating applied to the medical device 1 provides for an improved occlusion, improved sealing of a defect, such as a heart defect, an improved endothelialization and/or for slowing down the blood flow through the defect.

Figure 26B:
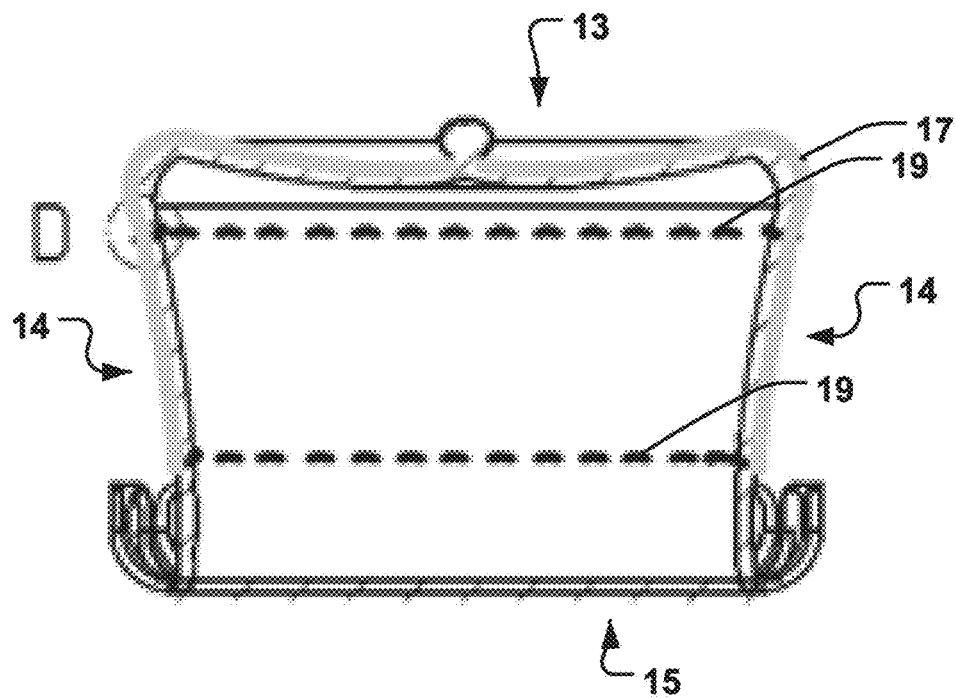
FIG. 26b is a lateral view of a medical implant with a non-fibrous membrane outside the medical implant.

In an embodiment according to FIG. 26*b*, a medical implant 1 is instead provided with a non-fibrous membrane 17 externally, i.e. on the outside of the medical implant 1. Such a non-fibrous membrane 17 may be sewed onto the medical implant 1 by stitching it onto the medical implant 1 along the medical implant's circumference with stitches 19. In some embodiments, the non-fibrous membrane 17 only covers one end 13, and not the side 14, of the medical implant 1. In another embodiment, the end 13 and the side 14 are provided with a non-fibrous membrane 17. In yet another embodiment, only the ends of the medical implant 1 are provided with a non-fibrous membrane 17, i.e. the end 13 and the other end 15 are provided with a non-fibrous membrane 17, whereas the side 14 is not provided with any non-fibrous membrane 17. Thereby, the medical implant is covered at both ends 13, 15. A non-fibrous membrane 17 applied to the medical device 1 provide for an improved occlusion, improved sealing of a defect, such as a heart defect, an improved endothelialization and/or for slowing down the blood flow through the defect. However, a coating 11 offers an advantage over the non-fibrous membrane 17, since there is no stitching, no sewing or even any clips needed for attaching and/or affixing the coating to the medical implant 1. Thus, the applying of a coating 11 instead of a non-fibrous membrane 17 may offer the advantage of providing easier and cheaper manufacturing. When compared to providing membranes or patches inside the medical implant 1, this advantage may be even greater, since the applying of membranes or patches inside such a medical implant 1 is even more time-consuming and complicated than just applying a non-fibrous membrane on an outside of the medical implant 1, because the membranes or patches has to first be put inside the medical implant 1 and then sewed or stitched onto the medical implant, while being inside the medical implant 1.

Figure 27A:
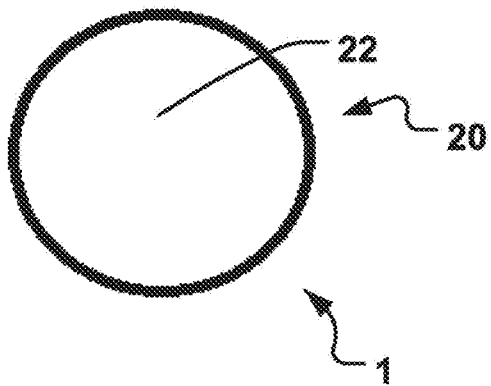
FIG. 27a is a top view of a medical implant.
Figure 27B:
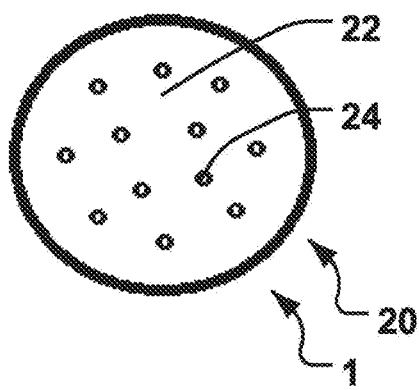
FIG. 27b is a top view of a medical implant having a coating with perforations evenly distributed.

According to an embodiment, depicted in FIG. 27*a*, one end 20 of the medical implant 1 is completely covered with a coating 22. Thus, an improved occlusion, an improved sealing of a defect, such as a heart defect, an improved endothelialization and/or a slowing down of the blood flow through the defect is achieved. However, in order to provide some body liquid to pass through the medical implant 1 once implanted, the coating may be provided with perforations or microperforations. This is shown in FIG. 27*b*, which depicts a situation where one end 20 of the medical implant 1 has been covered with a coating 22 and where the coating has been perforated, i.e. provided with perforations 24 or microperforations. Such perforations or microperforations may be provided by a process, such as mechanical perforation or laser perforation, i.e. laser cutting. The use of laser perforation offers the advantage of a better consistency of the hole size, i.e. the perforation size, than the use of mechanical perforation. By providing the coating 22 with perforations or microperforations, an initial controllable body liquid retention is enabled. Furthermore, the integration of the medical implant 1 may be enhanced and/or facilitated by the use of such perforations 24 or microperforations, since the body liquid is allowed to enter into the interior of the medical implant 1. A limited blood flow may actually pass through the medical implant 1 after implantation. However, this limited blood flow will gradually decline upon blood coagulation and/or endothelialization of the implanted medical implant. Thus, by the use of perforations 24 or microperforations, the occlusion is not abrupt, but formed gradually over time.

Figure 27C:
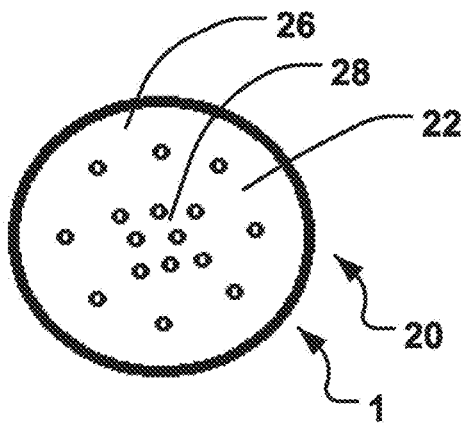
FIG. 27c is a top view of a medical implant having a coating with perforations, wherein the density of perforations in some areas is higher than the density of perforations in other areas.
Figure 27D:
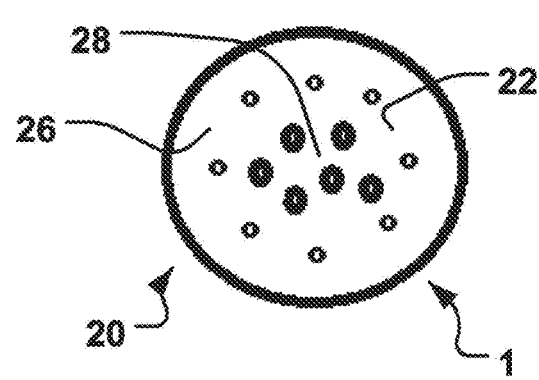
FIG. 27d is a top view of a medical implant having a coating with perforations, wherein a diameter of perforations in some areas is larger than a diameter of perforations in other areas.

In one embodiment, the perforations 24 or microperforations of the coating 22 are uniformly distributed over the area of the coating 22. However, in other embodiments, the perforations 24 or microperforations are randomly distributed. In yet another embodiment, depicted in FIG. 27*d*, a first central area 28 of the coating 22, corresponding to a first area of the medical implant is provided with perforations of a larger size, such as a diameter, than perforations of a second peripheral area 26 of the coating 22, corresponding to a second area of the medical implant 1, so that the inflow to different areas is controlled. As an alternative, the first central area 28 of the coating 22, corresponding to a first area of the medical implant 1, is provided with a higher number of perforations or a higher density of perforations than a second peripheral area 26 of the coating 22, corresponding to a second area of the medical implant, so that the inflow to different areas is controlled. This is depicted in FIG. 27*c*.

Figures 28, 32:
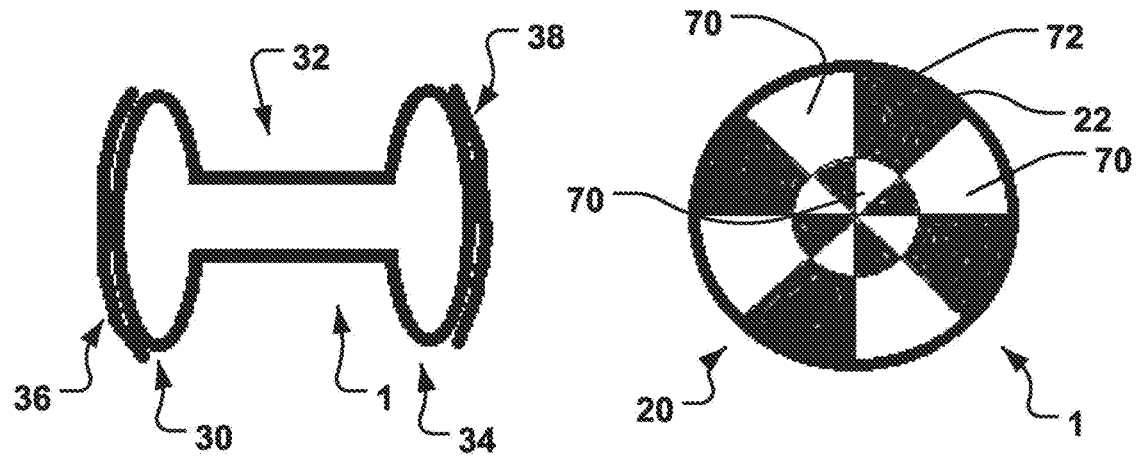
FIG. 28 is a lateral view of a medical implant, which has been provided with a coating at both ends.
FIG. 32 is a top view of a medical implant, provided with a coating, wherein the coating forms a pattern.

In FIG. 28, another kind of medical implant 1 or occluder is shown. This medical implant 1 comprises a first disc-shaped section 30, a tubular middle section 32 and a second disc-shaped section 34. In this embodiment, the one depicted in FIG. 28, only the ends of the medical implant 1 are coated or provided with non-fibrous membranes, i.e. the outer end side 36 of the first disc-shaped section 30 and the outer end side 38 of the second disc-shaped section 34 are coated or provided with non-fibrous membranes. The application of a coating can e.g. be performed by dipping both outer end sides 36, 38 into a solution, with a specific viscosity. Thereby, the medical implant is covered at both ends. In another embodiment, only the outer end side 36 of the first disc-shaped section 30 is provided with a coating 22. In yet another embodiment, the full length of the medical implant 1 is provided with a coating 22. In some embodiments, the tubular middle section 32 is provided with a coating 22, whereas the disc-shaped sections 34, 36 are not provided with a coating.

Figure 29:
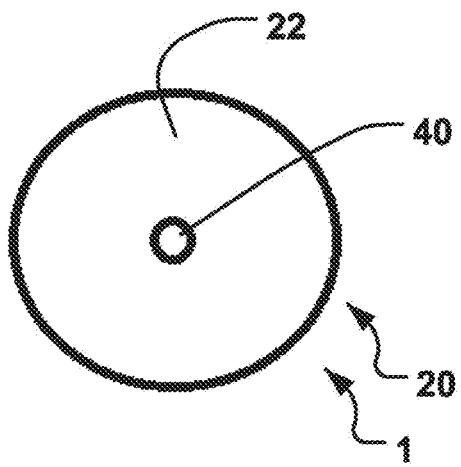
FIG. 29 is a top view of a medical implant with a coating covering only a part of the medical implant in a radial direction.

In yet another embodiment, depicted in FIG. 29, a coating 22 or non-fibrous film membrane is arranged at an end 20 of a medical implant 1 so as to obtain an inflow of blood, into the inner of the medical implant 1, after implantation and thus in an expanded shape, from a distal end of the medical implant 1 for enhancing integration of the medical implant with surrounding blood upon clotting thereof. This can e.g. be achieved by providing the end 20 with a coating 22, which covers substantially the whole end 20, but does not cover the section 40 of the end 20. Thus, an inflow of blood, into the inner of the medical implant 1 can be obtained through the section 40. The section 40 may be centred or situated at any other position at the end 20. As an alternative, the section 40 may instead by surrounding the coating 22, i.e. the coating 22 is applied only to a central portion of the end 20.

Figure 30:
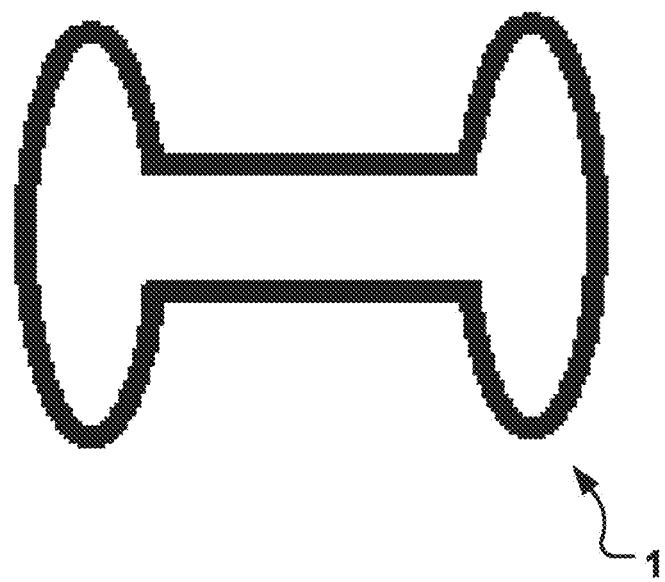
FIG. 30 is a lateral view of a medical implant in an expanded shape.
Figure 31:
FIG. 31 is a lateral view of a medical implant in a contracted shape.

FIG. 30 shows a medical implant 1 in an expanded shape. This is the shape the medical implant 1 preferably has after being implanted. This is also the shape, the medical implant resiliently returns to, i.e. it can also be called the relaxed shape. However, in order to deliver a medical implant 1 into a target site inside a mammal body, the medical implant 1 needs to be put through a narrow delivery catheter. In order for the medical implant 1 to fit into a narrow delivery catheter, the medical implant 1 will have to take on another shape. This other shape is here called the contracted shape. It could also be called a delivery shape. The medical implant in its contracted shape can be seen in FIG. 31. The coating 22 is in one embodiment applied to the medical implant 1, while the medical implant 1 is in the contracted shape. Thereby, the coating 22 will be prone to contribute to force the medical implant into its contracted shape and thus provide for facilitation of the delivery of the medical implant 1 through a catheter.

FIG. 32 is a top view of a medical implant, provided with a coating 22, wherein the coating 22 forms a pattern. Such a pattern can be any pattern, which is advantageous for control of a desired flow pattern through the medical implant 1 upon implantation. In the embodiment according to FIG. 32, the medical implant 1 is provided with a coating 22 in some sections, i.e. one section 72 of the end portion 20 of the medical implant 1 is provided with a coating 22, whereas all adjacent sections 70 are not provided with a coating and likewise all sections being adjacent to a non-coated section 70 are provided with a coating 22. By the use of such a pattern of covered sections 72 or cells an efficient control of a desired flow pattern through the medical implant 1 upon implantation is established. The sections or cells may be large and thus cover large portions of the medical implant or as small as a gap between adjacent strands of the mesh, which makes up the medical implant 1. The pattern may be formed be first applying a coating 22 by a method, such as dipping the medical implant 1 into a solution, and thereafter removing parts of the coating 22 so as to form a pattern of coating 22.

Figure 33:
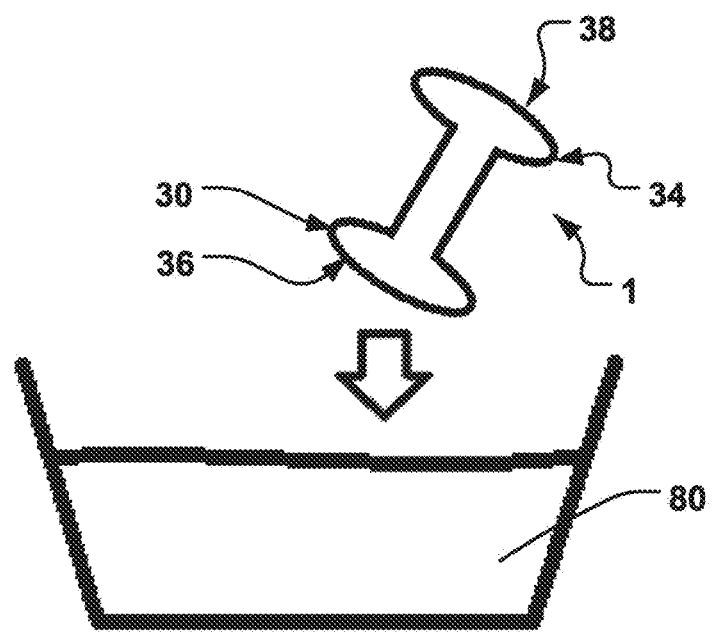
FIG. 33 is a lateral view of a medical implant being coated by dipping.

A step of a method of producing a medical implant for occluding an opening in a body is shown in FIG. 33, which is a lateral view of a medical implant being coated by dipping. In some embodiments, such a method comprises producing a body mesh of strands forming a plurality of adjacent cells delimited by the strands. Some or all of these cells may be provided with a coating. Therefore, in some embodiments, the method further comprises applying a polymer, such as polyurethane, polytetrafluoroethylene (PTFE) or expanded polytetrafluoroethylene (ePTFE), to at least part of an external surface of the medical implant 1, such as the outer end side 36 of the first disc-shaped section 30 of the medical implant 1. The use of e.g. PTFE or ePTFE may be especially advantageous, since these materials may provide for low friction. The polymer may be applied to the medical implant 1 by e.g. dipping, spraying, electro-spinning, electro-spraying or Nano-spinning. As another alternative, instead of coating the medical implant 1, a non-fibrous film membrane may be sewed onto the external surface of the medical implant 1. Such a non-fibrous film membrane may be manufactured by applying a film on a substrate and then removing the substrate. E.g. a film can be applied by dipping a substrate into a solution and thereafter removing the substrate. As an alternative, a substrate can be sprayed and thereafter removed from the coating formed by the spray, so that a non-fibrous film membrane is obtained.

In FIG. 33, the process of dipping a medical implant into a solution 80 of a specific viscosity is shown. Thus, the polymer is applied to the medical implant 1 by dipping the medical implant 1 into a solution 80 of a specific viscosity, so that a non-fibrous coating is applied and affixed to an external surface of the medical implant 1. In one embodiment only an outer end side 36 of a first disc-shaped section 30 of the medical implant is dipped into the solution. In another embodiment, the outer end side 36 of the first disc-shaped section 30 and an outer end side 38 of a second disc-shaped section 34 of the medical implant 1 are dipped into the solution. In other embodiments, further parts of the medical implant 1 may be dipped into the solution. As an example, the side 14 (shown in FIG. 27a) can be dipped into the solution. As another example, substantially the whole medical implant 1 may be dipped into the solution. Which parts of the medical implant 1 that are dipped into the solution may depend on what kind of medical device 1 is to be applied with coating, i.e. it may depend on whether the medical implant is e.g. an atrial septal defect (ASD) occluder, a Patent foramen ovale (PFO) occluder, a paravalvular leakage (PLD) occluder, a ventricular septal defect (VSD) occluder or some other medical implant.

Figure 34:
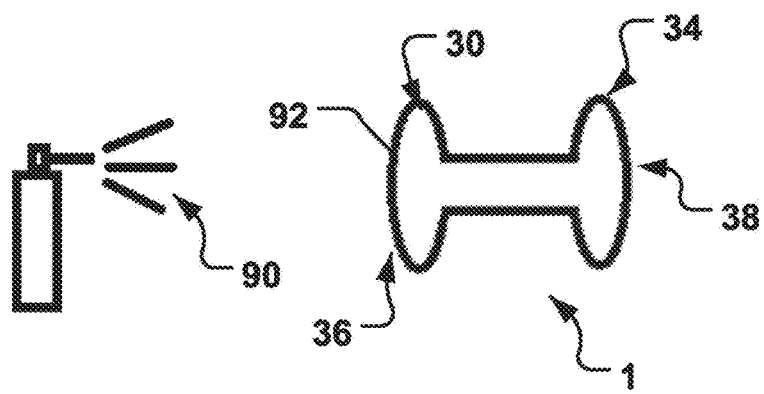
FIG. 34 is a lateral view of a medical implant being coated by spraying.

Alternatively, the coating can be applied to the medical implant 1 by spraying the medical implant with a spray 90, which is of a specific viscosity, so that a non-fibrous coating 92 is applied and affixed to an external surface of the medical implant 1. This alternative is shown in FIG. 34, which is a lateral view of a medical implant 1 being coated by spraying. In one embodiment only an outer end side 36 of a first disc-shaped section 30 of the medical implant is sprayed. In another embodiment, the outer end side 36 of the first disc-shaped section 30 and an outer end side 38 of a second disc-shaped section 34 of the medical implant 1 are sprayed. In other embodiments, further parts of the medical implant 1 may be sprayed. As an example, the side 14 (shown in FIG. 26a) can be sprayed. As another example, substantially the whole medical implant 1 may be sprayed. Which parts of the medical implant 1 that are sprayed may depend on what kind of medical device 1 is to be applied with coating, i.e. it may depend on whether the medical implant is e.g. an atrial septal defect (ASD) occluder, a Patent foramen ovale (PFO) occluder, a paravalvular leakage (PLD) occluder, a ventricular septal defect (VSD) occluder or some other medical implant.

Figure 35:
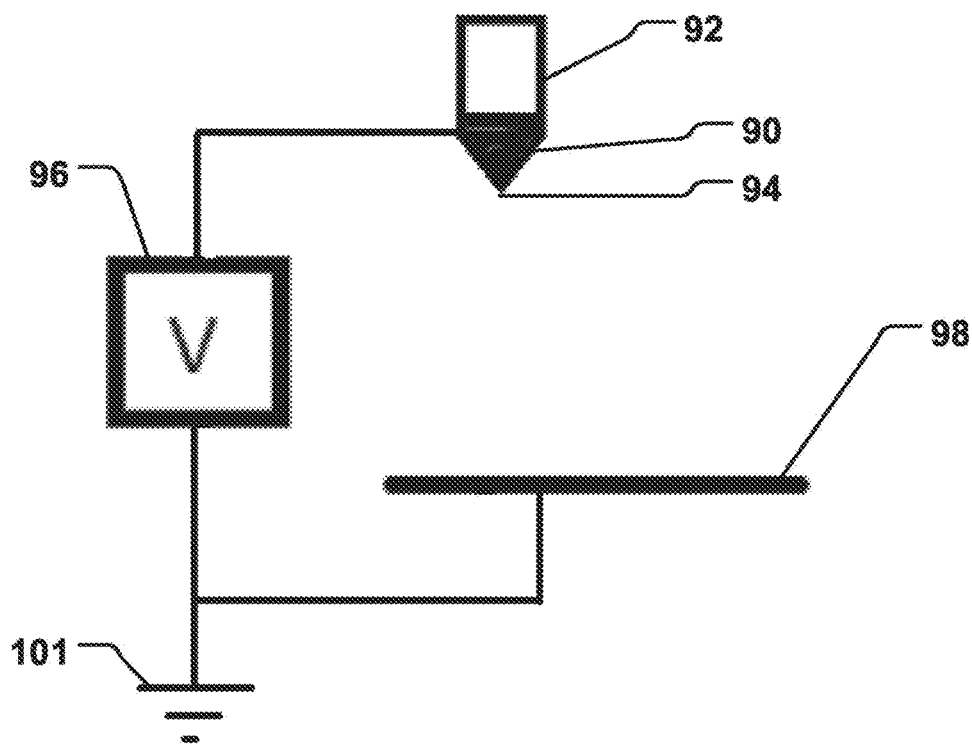
FIG. 35 is a schematic sketch of a medical implant being coated by a process, such as electro-spinning or Nano-spinning.

Other alternatives of applying a coating to the medical implant 1 are e.g. electro-spinning, electro-spraying or Nano-spinning. FIG. 35 is a schematic sketch of a medical implant being coated by a process, such as electro-spinning or Nano-spinning. In the figure, a polymer or composite solution 90 is contained in a syringe pump 92. The syringe pump 92 comprises a spinneret, such as a hypodermic syringe needle or a metallic needle, which is connected to a high-voltage direct current power supply 96. The direct current power supply 96 is also connected to ground 101 and on the ground side, a collector 98 is connected to the direct current power supply 96. The medical implant 1 to be coated would typically be placed in connection with the collector 98. The polymer solution 90 is loaded into the syringe 92 and extruded, as droplets, from the tip of the needle 94 at a constant rate by the syringe pump 92. A sufficiently high voltage must then be applied to the droplets, so that the droplets become charged. Since electrostatic repulsion counteracts the surface tension, the droplets are stretched: At a critical point, a stream of liquid erupts from the surface. This point of eruption is known as the Taylor cone. If the molecular cohesion of the liquid is sufficiently high, stream breakup does not occur and a charged liquid jet is formed. Alternatively, if stream breakup occurs, the droplets are instead electro-sprayed.

As the jet dries in flight, the mode of current flow changes from ohmic to convective as the charge migrates to the surface of the strand. The jet is then elongated by a whipping process caused by electrostatic repulsion initiated at small bends in the strand, until it is finally deposited on the grounded collector. The elongation and thinning of the strand resulting from this bending instability leads to the formation of uniform strands. Such uniform strands may have nanometer-scale diameters.

In some embodiments, a method of producing a medical implant for occluding an opening in a body comprises producing a body mesh of strands forming a plurality of adjacent cells delimited by the strands. The producing of a body mesh of strands may be performed by intertwining strands along a length of a 3D fabric for forming a primary 3D fabric structure. The intertwining may be non-continuous, such as interrupted along the length, for forming a secondary structure of the 3D fabric without intertwining. A round braiding machine may be used for forming the primary and secondary fabric structures. In one embodiment, the method may comprise connecting a first end of a strand to a bobbin of a round braiding machine with a plurality of bobbins and a second end of the strand to a diametrically opposing bobbin of the round braiding machine for a plurality of strands and arranging middle sections of the plurality of strands in a fixed sequence over a braiding head in a crisscrossed manner. It may further comprise starting a braiding procedure, halting the braiding procedure, placing a crown-shaped holder for holding a plurality of strand loops at the braiding head, bending remaining strand sections individually in the middle sections in order to form strand loops, introducing the remaining strand sections into a space between the braiding head and the crown-shaped holder from below, placing the strand loops over pins of the crown-shaped holder, routing the strand ends to the bobbins, attaching the strand ends to the bobbins, placing a ring on top of the crown-shaped holder for fixation of the strand loops, continuing the braiding procedure until an intended strand length has been braided, detaching the strand ends from the bobbins, attaching the strand ends to the ring with fixation means and/or treating the braided material, the ring and the crown-shaped holder thermally for shaping of the medical implant. It may also comprise welding the strand ends together, by at least partly melting a length of the plurality of strands to form a defined ball pivot. Thereby, shaping of loops can be made accurately, fastly and/or easily.

The medical implant 1 may also in one embodiment be constructed so that the ends of the medical implant 1 folds inwards for delivery, i.e. when the medical implant 1 is in its contracted shape, the coating 22 is on the inside and covered and/or protected by the sides of the medical implant 1, which sides are close to or touching the inside wall of a delivery catheter, in which it is delivered. The ends of the medical implant 1 are in this embodiment somewhat conically shaped or funnel-shaped, so that the medical implant 1 folds into its contracted shape with its coated ends covered on the outside with the sides of the medical device 1. The two disc-shaped sections 30, 34 of the medical device 1 may also be cupped away from each other.

The present disclosure has been described above with reference to specific embodiments. However, other embodiments than the above described are equally possible within the scope of the disclosure. Different method steps than those described above, may be provided within the scope of the disclosure. The different features and steps of the disclosure may be combined in other combinations than those described. The scope of the disclosure is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

The invention claimed is:

1. A method of manufacturing a 3D fabric of strands for forming an occluder, wherein said method comprises:
   intertwining a first length of said strands to form a first portion of a primary 3D fabric structure;
   interrupting said intertwining to form a plurality of non-intertwined strand loops of a secondary 3D fabric structure; and
   intertwining a second length of said strands to form a second portion of the primary 3D fabric structure after said interrupting.

2. The method of claim 1, comprising:
   connecting a first end of a strand to a bobbin of a round braiding machine with a plurality of bobbins and a second end of said strand to a diametrically opposing bobbin of said round braiding machine for a plurality of strands and arranging middle sections of said plurality of strands in a fixed sequence over a braiding head in a crisscrossed manner;
   starting a braiding procedure;
   halting said braiding procedure;
   placing a crown-shaped holder for holding a plurality of strand loops at said braiding head;
   bending remaining strand sections individually in said middle sections in order to form strand loops; introducing said remaining strand sections into a space between said braiding head and said crown-shaped holder from below;
   placing said strand loops over pins of said crown-shaped holder;
   routing said strand ends to said bobbins;
   attaching said strand ends to said bobbins;
   placing a ring on top of said crown-shaped holder for fixation of said strand loops;
   continuing said braiding procedure until an intended strand length has been braided;
   detaching said strand ends from said bobbins;
   attaching said strand ends to said ring with fixation means;
   treating said braided material, said ring and said crown-shaped holder thermally for shaping of said occluder;
   welding said strand ends together, by at least partly melting a length of said plurality of strands to form a defined ball pivot.

3. The method of claim 1, wherein forming said strand loops comprises forming said strand loops into a substantially non-planar three-dimensional shape, bent out of a direction perpendicular to a longitudinal axis of said occluder.

4. The method of claim 1, wherein said strand loops comprises strand loops of different sizes and shapes, and/or wherein said strand loops are arranged equidistantly around a perimeter of said secondary 3D fabric structure.

5. The method of claim 1, further comprising:
   intertwining, braiding, knitting or weaving together said strands to form a body mesh of strands comprising a plurality of adjacent cells delimited by said strands; and
   applying a polymer to at least part of an external surface of said body mesh, wherein said polymer is applied to said body mesh by dipping, spraying, electro-spinning, electro-spraying or Nano-spinning.

6. The method of claim 5, wherein said polymer is applied to said body mesh by dipping said body mesh into a solution of a specific viscosity so that a non-fibrous coating is applied and affixed to an external surface of said body mesh.

7. The method of claim 5, wherein said polymer is applied to said body mesh by spraying said body mesh with a spray having a specific viscosity so that a non-fibrous coating is applied and affixed to an external surface of said body mesh.

8. An occluder comprising;
 a primary structure having a first portion and a second portion of a plurality of strands intertwined to form a braided material, wherein the first portion is separate from the second portion; and
 a secondary structure having a plurality of non-intertwined strand loops formed of said plurality of strands, the plurality of non-intertwined strand loops positioned between said first portion and said second portion of said primary structure.

9. The occluder of claim 8, wherein said occlude is a left aurical appendix occlude and said braided material is shapeable as a frustum of a hollow cone-shaped cylinder and wherein said plurality of non-intertwined strand loops surround a rim of said hollow cone-shaped cylinder and are extendable outwardly from said hollow cone-shaped cylinder substantially perpendicularly to a center axis of said hollow cone-shaped cylinder.

10. The occluder of claim 9, wherein said plurality of non-intertwined strand loops are arranged in one or two rows all along said rim.

11. The occluder of claim 10, further comprising at least one membrane or coating for improved occlusion.

12. The occluder of claim 11, wherein said at least one membrane or coating is made of a biocompatible material.

13. The occluder of claim 9, further comprising:
 a coupling, formable as a ball pivot.

14. The occluder of claim 13, wherein said coupling is formed as a ball pivot by welding ends of said strands together.

15. The occluder of claim 13, wherein a proximal side of said braided material is shapeable as a concave shape to assure a sinking of the coupling when said occluder is compressed.

16. The occluder of claim 8, wherein said braided material comprises:
 a plurality of adjacent cells delimited by said plurality of strands,
 said body mesh having an external surface, and
 a coating covering said external surface for at least partly restricting a fluid flow through a structural tissue defect.

17. The occluder of claim 16, wherein said coating is provided with perforations or microperforations for enabling an initial controllable fluid retention.

18. The occluder of claim 17, wherein a first area of said coating corresponding to a first area of said occlude is provided with perforations of a larger size than perforations of a second area of said coating corresponding to a second area of said occluder so that the inflow to different areas is controlled or wherein a first area of said coating corresponding to a first area of said occluder is provided with a higher number of perforations than a second area of said coating, corresponding to a second area of said occluder so that the inflow to different areas is controlled.

19. The occluder of claim 18, wherein said coating covers substantially a full diameter of both ends of said occluder.

20. The occluder of claim 18, wherein said coating covers substantially a full expanded diameter of said occluder and/or wherein said coating covers substantially a full length of said occluder.

21. The occluder of claim 18, wherein said coating only covers a portion of a full expanded diameter of said occluder and/or wherein said coating only covers a portion of a full length of said occluder.

22. The occluder according to claim 16, wherein said coating is arranged so as to obtain an inflow of blood, into the inner of said occluder in an expanded shape, from a distal end of said occluder for enhancing integration of said occluder with surrounding blood upon clotting thereof.

23. The occluder according to claim 16, wherein said coating is applied to said occluder, while said occluder is in an expanded shape.

24. The occluder according to claim 16, wherein said coating is applied to said occluder, while said occluder is in a contracted shape.

25. The occluder according to claim 16, wherein said occluder is covered with said coating so that a pattern of covered cells is established for efficient control of a desired flow pattern upon implantation.

26. The occluder of claim 16, wherein said coating is made of a material consisting of Polyurethane (PU), Polytetrafluoroethylene (PTFE) or Expanded Polytetrafluoroethylene (ePTFE).

27. A kit for manufacturing an occluder with the method of claim 1, comprising:
 a plurality of strands for braiding;
 a braiding cylinder with a braiding head of an appropriate diameter, adaptable to a braiding machine;
 a crown-shaped holder having a plurality of pins for holding a plurality of strand loops; and
 a ring having holes corresponding to the plurality of pins of the holder for fixation of said strand loops.

* * * * *